United States Patent
Villa et al.

(10) Patent No.: US 6,773,720 B1
(45) Date of Patent: Aug. 10, 2004

(54) MESALAZINE CONTROLLED RELEASE ORAL PHARMACEUTICAL COMPOSITIONS

(75) Inventors: Roberto Villa, Panama (PA); Massimo Pedrani, Panama (PA); Mauro Ajani, Panama (PA); Lorenzo Fossati, Panama (PA)

(73) Assignee: Cosmo S.p.A., Milan (IT)

( * ) Notice: Subject to any disclaimer, the term of this patent is extended or adjusted under 35 U.S.C. 154(b) by 0 days.

(21) Appl. No.: 10/009,491

(22) PCT Filed: Jun. 8, 2000

(86) PCT No.: PCT/EP00/05321

§ 371 (c)(1),
(2), (4) Date: Dec. 13, 2001

(87) PCT Pub. No.: WO00/76481

PCT Pub. Date: Dec. 21, 2000

(30) Foreign Application Priority Data

Jun. 14, 1999 (IT) .......................................... MI99A1316

(51) Int. Cl.[7] ........................... A61K 9/127; A61K 9/14; A61K 9/22; A61K 9/26; A61K 9/52
(52) U.S. Cl. ........................ 424/450; 424/451; 424/452; 424/457; 424/464; 424/465; 424/468; 424/469; 424/484; 424/485; 424/488
(58) Field of Search .................................. 424/451, 452, 424/457, 464, 465, 467, 468, 469, 484, 485, 488, 450, 489, 490

(56) References Cited

U.S. PATENT DOCUMENTS

| | | | |
|---|---|---|---|
| 4,921,757 A | * 5/1990 | Wheatley et al. | 428/402.2 |
| 5,593,690 A | 1/1997 | Akiyama et al. | 424/457 |
| 5,851,555 A | 12/1998 | Sanghvi et al. | 424/464 |
| 5,911,980 A | * 6/1999 | Samour et al. | 424/70.17 |

FOREIGN PATENT DOCUMENTS

| | | |
|---|---|---|
| GB | 2 245 492 A | 1/1992 |
| WO | WO 98/26767 | 6/1998 |

* cited by examiner

*Primary Examiner*—Thurman K. Page
*Assistant Examiner*—S. Tran
(74) *Attorney, Agent, or Firm*—Young & Thompson

(57) ABSTRACT

Controlled-release oral pharmaceutical compositions containing as active ingredient 5-amino-salicylic acid, comprising: a) an inner lipophilic matrix consisting of substances with a melting point below 90° C. in which the active ingredient is at least partly inglobated; b) an outer hydrophilic matrix in which the lipophilic matrix is dispersed; c) optionally other excipients.

4 Claims, No Drawings

MESALAZINE CONTROLLED RELEASE ORAL PHARMACEUTICAL COMPOSITIONS

The present invention relates to controlled release oral pharmaceutical compositions containing as active ingredient 5-amino salicylic acid, also named mesalazine.

BACKGROUND OF THE INVENTION

Mesalazine is used in the treatment of Chron's disease and ulcerative colitis thanks to its antiinflammatory activity on the intestinal mucuses. Controlled-release formulations of mesalazine are disclosed in WO 95/16451, EP 0 453 001, EP 0 377 477.

The preparation of a sustained, controlled, delayed or anyhow modified release form can be carried out according to different known techniques:
1. The use of inert matrices, in which the main component of the matrix structure opposes some resistance to the penetration of the solvent due to the poor affinity towards aqueous fluids; such property being known as lipophilia.
2. The use of hydrophilic matrices, in which the main component of the matrix structure opposes high resistance to the progress of the solvent, in that the presence of strongly hydrophilic groups in its chains, mainly branched, remarkably increases viscosity inside the hydrated layer.
3. The use of bioerodible matrices, which are capable of being degraded by the enzymes of some biological compartment.

All the procedures listed above suffer, however, from drawbacks and imperfections.

Inert matrices, for example, generally entail non-linear, but esponential, release of the active ingredient.

Hydrophilic matrices have a linear behaviour until a certain fraction of active ingredient has been released, then they significantly deviate from linear release.

Bioerodible matrices are ideal to carry out the so-called "site-release", but they involve the problem of finding the suitable enzyme or reactive to degradation. Furthermore, they frequently release in situ metabolites that are not wholly toxicologically inert.

A number of formulations based on inert lipophilic matrices have been described: Drug Dev. Ind. Pharm. 13 (6), 1001–1022, (1987) discloses a process making use of varying amounts of colloidal silica as a porization element for a lipophilic inert matrix in which the active ingredient is incorporated.

The same notion of canalization of an inert matrix is described in U.S. Pat. No. 4,608,248 in which a small amount of a hydrophilic polymer is mixed with the substances forming an inert matrix, in a non sequential compenetration of different matrix materials.

EP 375,063 discloses a technique for the preparation of multiparticulate granules for the controlled-release of the active ingredient which comprises co-dissolution of polymers or suitable substances to form a inert matrix with the active ingredient and the subsequent deposition of said solution on an inert carrier which acts as the core of the device. Alternatively, the inert carrier is kneaded with the solution containing the inert polymer and the active ingredient, then the organic solvent used for the their dissolution is evaporated off to obtain a solid residue. The resulting structure is a "reservoir", i.e. is not macroscopically homogeneous along all the symmetry axis of the final form.

The same "reservoir" structure is also described in Chem. Pharm. Bull. 46 (3), 531–533, (1998) which improves the application through an annealing technique of the inert polymer layer which is deposited on the surface of the pellets.

To the "reservoir" structure also belong the products obtained according to the technique described in WO 93/00889 which discloses a process for the preparation of pellets in hydrophilic matrix which comprises:
dissolution of the active ingredient with gastro-resistant hydrophilic polymers in organic solvents;
drying of said suspension;
subsequent kneading and formulation of the pellets in a hydrophilic or lipophilic matrix without distinction of effectiveness between the two types of application.

EP 0 453 001 discloses a multiparticulate with "reservoir" structure inserted in a hydrophilic matrix. The basic multiparticulate utilizes two coating membranes to decrease the release rate of the active ingredient, a pH-dependent membrane with the purpose of gastric protection and a pH-independent methacrylic membrane with the purpose of slowing down the penetration of the aqueous fluid.

WO 95/16451 discloses a composition only formed by a hydrophilic matrix coated with a gastro-resistant film for controlling the dissolution rate of mesalazine.

When preparing sustained-, controlled-release dosage forms of a medicament topically active in the gastrointestinal tract, it is important to ensure a controlled release from the first phases following administration, i.e. when the inert matrices have the maximum release rate inside the logarithmic phase, namely the higher deviation from linear release.

Said object has been attained by the present invention, which also allows to prepare compositions characterized by a high content in active ingredient.

DISCLOSURE OF THE INVENTION

The invention provides controlled release oral pharmaceutical compositions containing 5-amino-salicylic acid as the active ingredient, comprising:
a) an inner lipophilic matrix consisting of substances with melting point below 90° C. in which the active ingredient is at least partially inglobated;
b) an outer hydrophilic matrix in which the lipophilic matrix is dispersed;
c) optionally other excipients.

DETAILED DISCLOSE OF THE INVENTION

The compositions of the invention can be obtained with a method comprising the following steps:
a) the active ingredient is first inglobated in a low melting excipient or mixture of excipients, while heating to soften and/or melt the excipient itself, which thereby incorporates the active ingredient by simple dispersion. After cooling at room temperature an inert matrix forms, which can be reduced in size to obtain matrix granules containing the active ingredient particles.
b) the inert matrix granules are subsequently mixed together with one or more hydrophilic water-swellable excipients.

This way, when the tablet is contacted with biological fluids, a high viscosity swollen layer is formed, which coordinates the solvent molecules and acts as a barrier to penetration of the aqueous fluid itself inside the new structure. Said barrier antagonizes the starting "burst effect" caused by the dissolution of the medicament inglobated inside the inert matrix, which is in its turn inside the hydrophilic matrix.

The lipophilic matrix consists of substances selected from unsaturated and/or hydrogenated fatty acids, salts, esters or amides thereof, fatty acids mono-, di- or triglycerids, waxes, ceramides, cholesterol derivatives or mixtures thereof having melting point within the range of 40 to 90° C.

If desired, a fatty acid calcium salt may be incorporated. in the lipophilic matrix which is subsequently dispersed in a hydrophilic matrix prepared with alginic acid, thus remarkably increasing the hydrophilic matrix viscosity following penetration of the solvent front until contact with the lipophilic matrix granules dispersed inside.

The weight content of the active ingredient in the lipophilic matrix usually ranges from 5 to 95%.

The inert lipophilic matrix is reduced into granules by an extrusion and/or granulation process, or any other known processes which retain the homogeneous dispersion and matrix structure of the starting mixture.

The hydrophilic matrix consists of excipients known as hydrogels, i.e. substances which pass from the dry state to the hydrated one, undergo the so-called "molecular relaxation", namely a remarkable increase in mass and weight following the coordination of a large number of water molecules by the polar groups present in the polymeric chains of the excipients themselves.

Examples of hydrogels which can be used according to the invention are compounds selected from polymers or copolymers of acrylic or methacrylic acid, alkylvinyl polymers, hydroxyalkyl celluloses, carboxyalkyl celluloses, polysaccharides, dextrins, pectins, starches and derivatives, natural or synthetic gums, alginic acid.

The lipophilic matrix granules containing the active ingredient are mixed the with hydrophilic compounds cited above in a weight ratio typically ranging from 100:0.5 to 100:20 (lipophilic matrix: hydrophilic matrix). Part of mesalazine can optionally be mixed with hydrophilic substances to provide compositions in which the active ingredient is dispersed both in the lipophilic and the hydrophilic matrix, said comoositions being preferably in the form of tablets, capsules and/or minitablets.

The compression of the mixture of lipophilic matrix, hydrogel-forming compounds and, optionally, active ingredient non inglobated in the lipophilic matrix, yields a macroscopically homogeneous structure in all its volume, namely a matrix containing a dispersion of the lipophilic granules in a hydrophilic matrix.

The tablets, capsules and/or minitablets obtainable according to the invention can optionally be subjected to known coating processes with a gastro-resistant film, consisting of for example polymers of methacrylic acids (Eudragit$^{(R)}$) or cellulose derivatives, such as cellulose acetophthalate.

The compositions of the invention can contain a high percentage of active ingredient compared with the total composition weight up to 95%, an advantageous characteristic in the case of mesalazine which requires rather high unitary doses.

In terms of dissolution characteristics, the compositions of the invention provide a release profile of the active ingredient more homogeneous than the traditional systems. In fact, the immediate penetration of water inside the superficial layer of the hydrophilic matrix and the consequent swelling due to the distension of the polymeric chains of the hydrogels, gives rise to a high viscosity hydrated front which prevents the further penetration of water, linearly slowing down the dissolution process to a well determined point which can be located at about half the thickness until the further penetration of water would cause the disintegration of the hydrophilic layer and therefore the release of the content which, consisting of lipophilic granules, however induces the diffusional mechanism typical of these structures and therefore further slows down the dissolution profile of the active ingredient.

The following examples illustrate the invention in greater detail.

EXAMPLE 1

770 g of 5-aminosalicylic acid are added in a kneader with 20 g of carnauba wax and 50 g of stearic acid with heating until homogeneous dispersion, then extruded into small granules while cold.

The inert matrix granules are loaded into a mixer in which 30 g of Carbopol 971P$^{(R)}$ and 65 g of hydroxypropyl methylcellulose are sequentially added.

After a first mixing step for homogeneously dispersing the powders, 60 g of microcrystalline cellulose and 5 g of magnesium stearate are added. After mixing, the final mixture is tabletted to unitary weight of 649 mg/tablet or 510 mg/tablet to obtain 500 and 400 mg dosages, respectively.

The resulting tablets are film-coated with cellulose acetophthalate or polymethacrylates and a plasticizer to provide gastric resistance and prevent the early release of product in the stomach.

The dissolution profile of these tablets shows the release of an active ingredient amount lower than 30% within the first hour of permanence in simulated enteric juice, an amount lower than 60% at the fourth hour and an amount lower than 90% at the eighth hour, thus proving that the double matrix effectively controls dissolution.

EXAMPLE 2

1000 g of 5-aminosalicylic acid are added in a kneader with 10 g of carnauba wax and 20 g of stearic acid with heating until homogeneous dispersion, then extruded into small granules while cold or directly granulated in a high rate mixer.

The resulting granules are loaded into a mixer in which 80 g of hydroxypropyl methylcellulose and 12 g of sodium starch glycolate are sequentially added. After a first mixing step, 11 g of silica colloidal and 11 g of magnesium stearate are added. The final mixture is homogenized, then tabletted to a unitary weight of 1144 mg/tablet.

The resulting tablets are then film coated with polymethacrylates or cellulose acetophthalate and plasticizers to provide gastric resistance.

The dissolution profile of these tablets after a lag time of permanence in the stomach and partly in the intestine provides the release of no more than 30% within the first hour, no more than 55% within two hours, no more than 70% within four hours, no more than 90% within eight hours.

EXAMPLE 3

850 g of 5-aminosalicylic acid are added in granulator/kneader with 9 g of beeswax and 22 g of palmitic acid with heating, until homogeneous dispersion; then worked to a granulate in a high shear granulating device. The resulting granules are then loaded into a mixer which is added in succession with 45.5 g of hydroxypropyl methylcellulose, 45.5 g of microcrystalline cellulose, 20 g of sodium starch glycolate, 22 g of colloidal silica and 22 g of magnesium stearate. After homogenization, the final mixture is tabletted to a unitary weight of 975 mg/tablet.

The resulting tablets are then film coated with polymethacrylates or acetophthalate of cellulose and plasticizers to provide gastric resistance.

The dissolution profile of these tablets after a lag time of permanence in the stomach and partly in the intestine provides the release of no more than 30% within the first hour, no more than 50% within two hours, no more than 70% within four hours, no more than 90% within eight hours.

EXAMPLE 4

1100 g of 5-aminosalicylic acid are added in granulator/kneader with 10 g of wax carnauba and 20 g of stearic acid.

10 g of polyacrylamide, 39.5 of microcrystalline cellulose and 22 g of colloidal silica are separately loaded into the homogenizer/granulator to obtain a homogeneous solid mixture, which is placed in the mixer where the active ingredient has been granulated and homogenized. 49.5 g of hydroxypropyl methylcellulose and 12 g of sodium alginate are thoroughly mixed, then added with 5 g of calcium carbonate, 34.5 g of microcrystalline cellulose and 11 g of magnesium stearate. The mixture is homogenized, then tabletted to a final unitary weight of 1194 mg/tablet. The resulting tablets are then film-coated with polymethacrylates or cellulose acetophthalate and plasticizers to provide gastric resistance.

The dissolution profile of these tablets after a lag time of permanence in the stomach and partly in the intestine provides the release of no more than 35% within the first hour, no more than 50% within two hours, no more than 70% within four hours, no more than 90% within eight hours.

EXAMPLE 5

1200 g of 5-aminosalicylic acid are added in mixer with 10 g of carnauba wax and 20 g of stearic acid, with heating until homogeneous dispersion, then cold extruded into small granules or directly granulated in the high rate mixer. The resulting granules are loaded into a mixer, then 70 g of hydroxypropyl methylcellulose and 20 g of sodium starch glycolate are sequentially added.

After a first mixing step, 80 g of sodium carbonate and 5 g of magnesium stearate are added. The final mixture is homogenized, then tabletted to unitary weight of 1375 mg/tablet.

The resulting tablets are then film-coated with polymethacrylates or cellulose acetophthalate and plasticizers to provide gastric resistance.

The dissolution profile of these tablets after a lag time of permanence in the stomach and partly in the intestine provides the release of no more than 30% within the first hour, no more than 50% within two hours, no more than 70% within four hours, no more than 90% within eight hours.

What is claimed is:

1. Controlled-release oral pharmaceutical compositions containing as an active ingredient 5-amino-salicylic acid, comprising:
   a) an inner lipophilic matrix consisting of substances selected from the group consisting of unsaturated and/or hydrogenated fatty acid, salts, esters or amides thereof, fatty acid mono-, di- or triglycerids, waxes, ceramides, and cholesterol derivatives with melting points below 90° C., and wherein the active ingredient is dispersed both in said the lipophilic matrix and in the hydrophilic matrix;
   b) an outer hydrophilic matrix wherein the lipophilic matrix is dispersed, and said outer hydrophilic matrix consists of compounds selected from the group consisting of polymers or copolymers of acrylic or methacrylic acid, alkylvinyl polymers, hydroxyalkyl celluloses, carboxyalkyl celluloses, polysaccharides, dextrins, pectins, starches and derivatives, alginic acid, and natural or synthetic gums;
   c) optionally other excipients;
   wherein the active ingredient is present in an amount of 80 to 95% by weight of the total composition, and wherein the active ingredient is dispersed both in the lipophilic matrix and in the hydrophilic matrix.

2. Compositions as claimed in claim 1, wherein 5-aminosalicylic acid is dispersed in a molten lipophilic matrix by kneading, extrusion and/or granulation.

3. Compositions as claimed in claim 1, in the form of tablets, capsules, mintablets.

4. A process for the preparation of the compositions of claim 1, which comprises:
   a) melt granulation of at least one portion of the active ingredient with the lipophilic excipients with melting point lower than 90° C.;
   b) mixing the granules from step a) with the hydrophilic excipients and subsequent tabletting or compression.

* * * * *